United States Patent [19]
Mank et al.

[11] Patent Number: 5,503,851
[45] Date of Patent: Apr. 2, 1996

[54] MICROENCAPSULATION OF WATER-SOLUBLE MEDICAMENTS

[75] Inventors: Reinhard Mank, Kiel-Russee; Jan Gustafsson, Kiel; Joachim Hörig, Kiel-Kronshagen; Wolfgang Köchling, Tüttendorf; Birgit Nerlich, Kiel-Russee, all of Germany

[73] Assignee: Ferring Arzneimittel GmbH, Kiel, Germany

[21] Appl. No.: 84,592

[22] Filed: Jul. 1, 1993

[30] Foreign Application Priority Data

Jul. 10, 1992 [DE] Germany .......... 42 23 169.8

[51] Int. Cl.$^6$ ..................... A61K 9/16
[52] U.S. Cl. ............ 424/489; 424/501; 424/502
[58] Field of Search ............... 424/489, 501, 424/502

[56] References Cited

U.S. PATENT DOCUMENTS

| | | | |
|---|---|---|---|
| 4,164,573 | 8/1979 | Galinsky | 424/178 |
| 4,908,210 | 3/1990 | Adams | 424/489 |
| 5,208,038 | 5/1993 | Gressani et al. | 424/501 |

FOREIGN PATENT DOCUMENTS

| | | |
|---|---|---|
| 0292710 | 11/1988 | European Pat. Off. . |
| 0377477 | 11/1990 | European Pat. Off. . |
| 3201411C2 | 8/1982 | Germany . |
| 3822459A1 | 3/1989 | Germany . |

Primary Examiner—James J. Seidleck
Assistant Examiner—John M. Cooney, Jr.
Attorney, Agent, or Firm—Nixon & Vanderhye

[57] ABSTRACT

In a process for the microencapsulation of water-soluble active ingredients according to the principle of phase separation, which comprises the steps (a) Preparation of a solution of a biocompatible polymer in an organic solvent;

(b) Addition of an aqueous solution of one or more active ingredients or dispersion of one or more solid active ingredients in the solution from stage (a);

(c) Addition of a coacervation agent to the emulsion or dispersion from stage (b);

(d) Introduction of the mixture from stage (c) into an excess of a hardening agent;

(e) Collection and washing of the microcapsules, natural or synthetic esters of saturated $C_4$ to $C_{18}$ carboxylic acids and polyhydric alcohols are used as hardening agents.

20 Claims, No Drawings

MICROENCAPSULATION OF WATER-SOLUBLE MEDICAMENTS

The invention relates to a process for the microencapsulation of water-soluble active ingredients by phase separation and particularly the hardening of the microcapsules.

The microencapsulation of pharmaceutical active ingredients with biocompatible polymers is suitable for the production of compositions with controlled release behaviour. The microencapsulation of pharmaceutical active ingredients by phase separation is generally accomplished by the following steps:

(a) Preparation of a solution of the polymer in an organic solvent which is not miscible with water;

(b) Addition of an aqueous solution of the active ingredient or dispersing of the solid active ingredient in the polymer solution;

(c) Addition of a so-called non-solvent (coacervation agent), i.e. an organic liquid which is miscible with the first organic solvent and in which the polymer used is not soluble. The addition of the coacervation agent leads to phase separation and therefore to the formation of embryonic or crude capsules;

(d) Hardening of the crude capsules by incorporation of the mixture from stage (c) into a hardening agent which has the function of extracting the polymer solvent from step (a) from the microcapsules;

(e) Removing, washing and drying of the hardened microcapsules.

Various solvents have been described for the hardening of microcapsules. The hardening of microcapsules with saturated liquid hydrocarbons, such as e.g. hexane, heptane, cyclohexane or petroleum ether is, for example, described in EP-A-52 510 and in EP-A-172 422. It has, however, been shown that liquid hydrocarbons cannot be completely removed from the microcapsules after hardening. The heptane content of hardened microcapsules is typically 5 to 15% and thereby in many cases exceeds the active ingredient content of these capsules. In addition, liquid hydrocarbons are flammable, meaning that their processing requires strict safety precautions.

In order to avoid these disadvantages, other solvents were used as hardeners. Described in DE-A-35 36 902 is the hardening of microcapsules with fluorine hydrocarbons or fluorine-halogen hydrocarbons. These compounds are, however, also not completely removable from the hardened microcapsules; it was, moreover, shown in EP-A-377 477 that such solvents are not suitable for all polymers. Furthermore, fluorine or fluorine-halogen hydrocarbons are problematical from an ecological viewpoint, which is documented in a drastic reduction of the application of these substances by the legislators.

U.S. Pat. No. 5,000,886 describes the hardening of microcapsules with volatile silicone oils, such as octamethyl cyclotetrasiloxane. These substances are not flammable, have only a low toxicity and can be removed by vacuum drying after the hardening of the capsules. In this way, a very low residual concentration of the hardener can be obtained in the micro-capsules. Such silicone oils are however not biologically degradable and are therefore only to a limited extent suitable for the production of microcapsules for parenteral application.

EP-A-377 477 relates to the hardening of microcapsules with ethyl and isopropyl esters of straight-chain $C_{12}$ to $C_{18}$ fatty acids. These compounds are distinguished by a low toxicity in mice and are therefore regarded as fully biocompatible. However, because of their relatively high solidification point in most cases, they show disadvantages in the processing.

It is the object of the invention to provide new agents for the hardening of microcapsules. These agents are to be biocompatible and biologically degradable, have a low toxicity and avoid the aforementioned disadvantages of known hardening agents. In addition, they should permit the control of the release behaviour of the microcapsules in a simple way.

The term "microcapsule" as used herein includes true microcapsules, i.e. microparticles in which an active ingredient is enclosed by a polymeric matrix, but also monolithic microcapsules (microspheres) in which an active ingredient is homogeneously distributed in a polymeric matrix. Under the conditions prevailing in the organism, biologically degradable compounds are completely degraded by means of hydrolysis and/or action of enzymes to non-toxic products and resorbed.

It was surprisingly found that this object can be achieved by using natural and synthetic esters of saturated $C_4$ to $C_{18}$ acids with polyhydric alcohols as hardening agents. These esters distinguish themselves by excellent properties in the hardening of crude capsules which were obtained according to the principle of phase separation. Furthermore, it was completely unexpectedly found that the release behaviour of microcapsules can also be influenced by controlling the content of the hardener in the capsules. The esters according to the invention of polyhydric alcohols show a very low toxicity and are in most cases completely biologically degradable. These compounds are not readily flammable and are completely unproblematical from an ecological viewpoint. The microcapsules prepared by the process according to the invention are free from alkanes, halogenated hydrocarbons and other biologically non-degradable solvents.

For the microencapsulation of pharmaceutical active ingredients, a biocompatible polymer is dissolved in an organic solvent (polymer solvent) which is not miscible with water. Biologically degradable as well as biologically non-degradable polymers can be used as biocompatible polymers. While biologically non-degradable polymers are primarily suitable for oral application, biologically degradable polymers are mainly used for parenteral or oral application.

Particularly suitable biologically degradable polymers are poly-L-lactide, poly-D,L-lactide and lactide-glycolide copolymers of varying composition, particularly poly-D,L-lactide coglycolides with a molar ratio of 10:90 (PLG 10/90) to 90:10 (PLG 90/10). Mixtures of the named polymers may also be used. Halogenated hydrocarbons such as $CH_2Cl_2$ or $CHCl_3$ are examples of the polymer solvent.

The pharmaceutical active ingredient to be encapsulated is either dispersed directly in the solution of the polymer or added in form of an aqueous solution to the polymer solution. The process according to the invention is suitable for the microencapsulation of water-soluble substances and preferably those which are biologically active. Examples of such biologically active substances are hormones and hormone release factors as well as hormone antagonists, analgesics, antiepileptics, cytostatics, antipyretics, chemo-therapeutics, narcotic-antagonists and sedatives. Particularly suitable active ingredients are amino acids, peptides and proteins, with and without additional non-protein proportion. These include for example the gonadotropin-releasing-hormone (GnRH) and its analogues (agonists and antagonists), calcitonin, growth hormone and hormone of the release of growth hormone, somatostatin and its analogues, parathyroid hormone (PTH) and its short-chain analogues.

Also suitable are gene products and gene (DNA) and RNA fragments.

A coacervation agent which effects a phase separation and leads to the precipitation of the polymer is added to the dispersion or emulsion of the active ingredient in the polymer solution.

Suitable as coacervation agent are solvents or solvent mixtures or a second non-compatible polymer which are/is miscible with the polymer solvent but do/does not dissolve the polymer. Examples of suitable coacervation agents are mineral or vegetable oils, neutral oils or silicon oils. The crude or embryonic capsules formed in this stage are hardened in the following process step.

For the hardening, the mixture of the embryonic capsules is introduced slowly with stirring into an excess of the hardening agent. The function of the hardening agent is to extract the polymer solvent and the coacervation agent from the formed microcapsules without dissolving the polymer or the active ingredient. The microcapsules are then separated from the hardening agent and washed.

Used according to the invention as hardening agents are natural or synthetic esters of saturated $C_4$ to $C_{18}$ carboxylic acids with polyhydric alcohols (natural oils, fatty oils). Preferred are fatty acids with a chain length of 8 to 18 and particularly preferably of 8 to 10 C atoms, such as for example caprylic acid and capric acid. Preferred alcohols are the di- and trihydric alcohols and particularly preferred are di- and trihydric alcohols with 2 to 4 C atoms, for example ethylene glycol, propylene glycol and glycerol. The hydroxyl groups of the alcohols can be esterified with the same or different fatty acids. The neutral oils include, inter alia, the esters of medium-chain fatty acids with di- or trihydric alcohols supplied under the trade name Miglyol®. Typical representatives of fatty oils are peanut, sesame and olive oils.

The ratio of the volume of hardening agent to the total volume of polymer solvent and coacervation agent can be varied within wide ranges. The hardening agent is normally used in excess, ratios of 10:1 to 30:1 being preferred. The hardening time is about 30 minutes to 2 hours, but other times are also possible.

The process according to the invention is especially suitable for the production of microcapsules with a diameter of 0.1 to 2000 μm, but the production of particles with smaller or larger diameters is also possible.

The hardening agents used according to the invention have the advantage that they display not only excellent hardening properties but that in addition they are completely unproblematical from a physiological viewpoint, as they are clinically tested oils. They are biologically degradable and are therefore also suitable as suspension agents for the final microcapsules. The use of the same agent both as hardener and as suspension agent facilitates re-suspension of the microparticles and therefore makes the addition of auxiliary agents, such as surfactants, superfluous. It is, however, possible to suspend the microcapsules produced by the process according to the invention in aqueous solvents. In addition, the oils according to the invention prevent agglomeration of the microcapsules and thus have a positive influence both on the application and on the distribution in the organism. Furthermore, a stable suspension during application is obtained by the oils used according to the invention. Particularly advantageous is the fact that the microcapsules can be provided in the form of ready-to-use suspensions. The neutral oils described are completely inert vis-a-vis active ingredients and auxiliaries; they are furthermore not oxidised by atmospheric oxygen and thus distinguish themselves by a high stability; and they are liquid at low temperatures and therefore easily processable. With fatty oils, the specifications given in the pharmacopoeia for a parenteral application should be observed.

A particular advantage of the process according to the invention is that the release behaviour of the active ingredients contained in the microcapsules can selectively be controlled by the oils used as hardening agents. Heretofore, control of the release behaviour was achieved by polymer-specific properties and the process technology.

The process according to the invention allows control of active ingredient release via, on the one hand, the viscosity of the oils used, and on the other, via the residual content of the oils in the microcapsules. While a high residual content of the oils used for hardening in the microcapsules prevents a rapid penetration of water into the capsules and therefore a dissolving of the water-soluble active ingredients, a reduction in the residual oil content in the capsules facilitates the penetration of water into the microcapsules and the dissolving of the active ingredients. This control of the release behaviour is possible since the oils used as hardening agents according to the invention are biocompatible, biologically degradable and completely unproblematical from a toxicological viewpoint, meaning that, in contrast to known hardening agents, the content of the hardening agent in the capsules does not have to be reduced to the lowest possible degree. The release of the active ingredients can be controlled with respect to time, for example, set to a period of one month or longer.

The oil content of the microcapsules can selectively be adjusted by washing the hardened microcapsules with a solvent. Suitable amongst others as solvent are alcohols, isopropanol being preferred.

As mentioned above, the hardening agents according to the invention are also suitable as coacervation agents. By using the same substance as coacervation, hardening and suspending agent, the content of undesirable substances in the microcapsules can be drastically reduced.

The invention is described in the following with reference to examples.

EXAMPLE 1

For microencapsulation the GnRH analogue triptorelin acetate (D-Trp$^6$-LHRH) was used as model active ingredient. 4.4 g poly (D,L-lactide-co-glycolide), molar ratio 50:50 (PLG 50/50) are dissolved in 120 ml methylene chloride and introduced into a reaction vessel equipped with a stirrer. 0.18 g triptorelin acetate are suspended in the polymer solution at a stirring speed of 500 revolutions/min, then 54 g silicone oil (Dow Corning 360 Medical Fluid®) are added with continued stirring at a rate of about 4.5 g/min. After addition of the silicone oil is completed, the mixture containing the crude microcapsules is introduced continually in a thin jet with continuous stirring at 1000 revolutions/min into 4 l of a caprylic-capric acid-triglyceride (Miglyol® 812, viscosity 27 to 33 mPa.s at 20° C.). Hardening of the microcapsules takes place within a period of 60 minutes. The thus-obtained microcapsules are filtered off, washed twice with isopropanol and dried.

The active ingredient content of the microcapsules is determined at 2.8% and the oil content at 10%. The particle diameter is 1 to 150 μm.

For the investigation of the in-vitro release behaviour, 90 mg of the microcapsules are suspended at 37° C. in 20 ml of 120 mMol phosphate buffer (pH 7.4, 0.1% NAN$_3$, 0.1% Polyethylene (20) sorbitanmonolaurat. (Tween®80)). After 6 hours, 4.7% of the active ingredient contained in the microcapsules are released, after 24 hours 11.2% and after 144 hours 38.9%.

EXAMPLE 2

Microcapsules are prepared according to example 1. with the exception that, for the hardening, a propylene glycol ester of caprylic/capric acid is used (Miglyol® 840, viscosity 8 to 14 mPa.s at 20° C.).

The oil content of the microcapsules prior to washing with isopropanol is 33.3% and after one wash with isopropanol 10.7%.

The investigation of the in-vitro release behaviour of the washed particles leads to the following results:

6 h: 35.3%

24 h: 57.3%

144 h: 67.2%

In the in-vitro model in rats, the microcapsules with the various oils showed a clear testosterone suppression over 28 days. This effect was intensified even further on using the oils as suspending agent.

EXAMPLE 3

Microcapsules are prepared according to example 1 with sesame oil (pharmacopoeia quality) being used as hardening agent. The volume of hardening agent is reduced to 2 l.

EXAMPLE 4

Microcapsules are prepared according to example 1 with PLG 75/25 or poly-D,L-lactide being used as polymer.

EXAMPLE 5

Microcapsules are prepared according to example 1 with Miglyol® 840 (a propylene glycol ester of caprylic/capric acid) being used as coacervation agent in place of the silicone oil.

We claim:

1. A process for the microencapsulation of water-soluble active ingredients according to the principle of phase separation which comprises the steps of:

a) preparing a solution of a biocompatible polymer in an organic solvent;

b) adding an aqueous solution of one or more active ingredients to or dispersing one or more solid active ingredients in the solution from stage (a);

c) adding a coacervation agent to the emulsion or the dispersion from stage (b) forming microcapsules in the solution;

d) introducing the mixture from stage (c) into an excess of a liquid, non-hydrogenated hardening agent; and e) separating the microcapsules from the hardening agent, collecting and washing the microcapsules to remove substantially all of the hardening agent, wherein liquid, non-hydrogenated natural or synthetic esters of saturated $C_4$ to $C_{18}$ carboxylic acids and polyhydric alcohols are used as hardening agent in an excess amount of up to 30 times the total volume of polymer solvent and coacervation agent.

2. A process according to claim 1, wherein esters of $C_8$ to $C_{18}$ fatty acids are used.

3. A process according to claim 1, wherein esters of $C_8$ to $C_{10}$ fatty acids are used.

4. A process according to claim 3, wherein esters of caprylic and/or capric acid are used.

5. A process according to claim 1, wherein esters of di- or trihydric alcohols are used.

6. A process according to claim 5, wherein esters of ethylene glycol, propylene glycol or glycerin are used.

7. A process according to claim 1, wherein esters are used in which the hydroxyl groups of the alcohols are esterified with the same or different fatty acids.

8. A process according to claim 1, wherein neutral oils or fatty oils are used as esters.

9. A process according to claim 8, wherein sesame oil or peanut oil are used as fatty oils.

10. A process according to claim 9, wherein biocompatible, biologically non-degradable or biologically degradable polymers are used.

11. A process according to claim 10, wherein poly-L-lactide, poly-D, L-lactide, lactide/glycolide copolymer or mixtures thereof are used as polymer.

12. A process according to claim 11, wherein a lactide/glycolide copolymer with a molar ratio of lactic acid to glycolic acid of 10:90 to 90:10 is used.

13. A process according to claim 1, wherein said hardening agent is used in an amount of 10 to 30 times the total volume of polymer solvent and coacervation agent.

14. A process according to claim 1, wherein the content of said hardening agent in the microcapsules is selectively changed by washing with a solvent and the active ingredient release is thereby controlled.

15. A process according to claim 14, wherein alcohols are used as said solvent.

16. A process according to claim 15, wherein isopropanol is used as said alcohol.

17. A process according to claim 1, wherein pharmaceutical active ingredients are used as said active ingredients.

18. A process according to claim 17, wherein amino acids, peptides, proteins or hormones are used as said pharmaceutical active ingredients.

19. A process according to claim 18, wherein gonadotropin-releasing-hormone (GnRH) or an analogue (agonist or antagonist), calcitonin, growth hormone or hormone for the release of growth hormone, somatostatin or an analogue, parathyroid hormone (PTH) or a short-chain analogue is used as said pharmaceutical active ingredient.

20. A process according to claim 1, wherein the same substance which is used as said hardening agent is also employed as said coacervation agent.

* * * * *